United States Patent
Amurthur et al.

(10) Patent No.: US 7,925,342 B2
(45) Date of Patent: Apr. 12, 2011

(54) IMPLANTABLE DEVICE FOR RESPONSIVE NEURAL STIMULATION THERAPY

(75) Inventors: Badri Amurthur, Edina, MN (US); Imad Libbus, St. Paul, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 685 days.

(21) Appl. No.: 11/539,289

(22) Filed: Oct. 6, 2006

(65) Prior Publication Data

US 2008/0086181 A1    Apr. 10, 2008

(51) Int. Cl.
*A61N 1/32* (2006.01)
(52) U.S. Cl. .......................................................... 607/2
(58) Field of Classification Search ............... 607/2, 42, 607/46
See application file for complete search history.

(56) References Cited

U.S. PATENT DOCUMENTS

| | | | | |
|---|---|---|---|---|
| 6,141,590 | A * | 10/2000 | Renirie et al. ................. 607/20 |
| 7,277,761 | B2 * | 10/2007 | Shelchuk ....................... 607/62 |
| 2005/0143779 | A1 | 6/2005 | Libbus | |
| 2006/0058852 | A1 * | 3/2006 | Koh et al. ........................ 607/42 |
| 2006/0206154 | A1 * | 9/2006 | Moffitt et al. ..................... 607/9 |
| 2006/0271118 | A1 * | 11/2006 | Libbus et al. .................... 607/9 |

FOREIGN PATENT DOCUMENTS

| | | |
|---|---|---|
| EP | 1486232 A2 | 12/2004 |
| WO | WO-03/018108 A2 | 3/2003 |
| WO | WO-2008/042476 A1 | 4/2008 |

OTHER PUBLICATIONS

"PCT Application No. PCT/US2007/070180, International Search Report mailed Nov. 30, 2007", 5 pgs.
"PCT Application No. PCT/US2007/070180, Written Opinion mailed Nov. 30, 2007", 8 pgs.
Davidson, N. S., et al., "Respiratory Modulation of Baroreceptor and Chemoreceptor Reflexes Affecting Heart Rate and Cardiac Vagal Efferent Nerve Activity", *Journal of Physiology*, 259(2), (1976), 523-530.

* cited by examiner

*Primary Examiner* — Scott M Getzow
*Assistant Examiner* — Amanda Patton
(74) *Attorney, Agent, or Firm* — Schwegman, Lundberg & Woessner, P.A.

(57) ABSTRACT

Described herein are methods and devices that utilize electrical neural stimulation to treat heart failure by modulating a patient's autonomic balance in a manner that inhibits sympathetic activity and/or augments parasympathetic activity. In one embodiment, the duty cycle for delivering neural stimulation is adjusted in accordance with one or more measured physiological variables.

20 Claims, 5 Drawing Sheets

IMPLANTABLE DEVICE FOR RESPONSIVE NEURAL STIMULATION THERAPY

FIELD OF THE INVENTION

This patent application pertains to methods and apparatus for the treatment of disease with electro-stimulatory therapy.

BACKGROUND

Heart failure (HF) refers to a clinical syndrome in which an abnormality of cardiac function causes a below normal cardiac output that can fall below a level adequate to meet the metabolic demand of peripheral tissues. It can be due to a variety of etiologies with ischemic heart disease being the most common. In patients with heart failure or following a myocardial infarction (MI) or other cause of decreased cardiac output, a complex remodeling process of the ventricles occurs that involves structural, biochemical, neurohormonal, and electrophysiologic factors. Ventricular remodeling is triggered by a physiological compensatory mechanism that acts to increase cardiac output due to so-called backward failure which increases the diastolic filling pressure of the ventricles and thereby increases the so-called preload (i.e., the degree to which the ventricles are stretched by the volume of blood in the ventricles at the end of diastole). An increase in preload causes an increase in stroke volume during systole, a phenomena known as the Frank-Starling principle. When the ventricles are stretched due to the increased preload over a period of time, however, the ventricles become dilated. As the heart begins to dilate, afferent baroreceptor and cardiopulmonary receptor signals are sent to the vasomotor central nervous system control center, which responds with hormonal secretion and sympathetic discharge. It is the combination of hemodynamic, sympathetic nervous system and hormonal alterations (such as presence or absence of angiotensin converting enzyme (ACE) activity) that ultimately account for the deleterious alterations in cell structure involved in ventricular remodeling. The sustained stresses causing hypertrophy induce apoptosis (i.e., programmed cell death) of cardiac muscle cells and eventual wall thinning which causes further deterioration in cardiac function. It has been shown that the extent of ventricular remodeling is positively correlated with increased mortality in post-MI and heart failure patients.

Ventricular remodeling in post-MI and HF patients is partly a function of an autonomic imbalance where there is in an increased level of sympathetic activity relative to parasympathetic activity. A similar autonomic imbalance exits in patients suffering hypertension and may be a factor in the development and progression of the disease. Long-standing hypertension is also a common cause of heart failure.

DETAILED DESCRIPTION

As noted above, activity of the autonomic nervous system is at least partly responsible for the ventricular remodeling which occurs as a consequence of an MI or heart failure due to other causes and may also contribute to hypertensive disease. All of these conditions can be treated by pharmacological intervention with the use of, for example, ACE inhibitors and beta-blockers. Pharmacological treatment carries with it the risk of side effects, however, and it is also difficult to modulate the effects of drugs in a precise manner. Described herein are methods and devices that employ electrical neural stimulation to modulate autonomic activity and which allow titration of the neural stimulation therapy in accordance with physiological measurements reflective of autonomic activity.

As described below, an implantable medical device may be equipped with a pulse generator for delivering electrical stimulation to one or more selected neural sites via appropriately positioned electrodes. In order to treat cardiac remodeling and/or hypertensive disease, the neural stimulation is applied in a manner that results in parasympathetic stimulation and/or sympathetic inhibition. Such neural stimulation may be delivered directly to an efferent parasympathetic nerve such as the vagus nerve or to an afferent nerve such as a baroreceptor that causes parasympathetic stimulation and/or sympathetic inhibition via a reflex arc. The vagus nerve provides parasympathetic stimulation to the heart which counteracts the effects of increased sympathetic activity, and stimulation of the vagus nerve at either a pre-ganglionic or post-ganglionic site produces dilation of the coronary arteries and a reduced workload on the heart. Vagal stimulation may be delivered, for example, using an intravascular electrode disposed near the vagus (e.g., in the internal jugular vein) or using a nerve cuff electrode (e.g., placed around the cervical vagus nerve bundle). Baroreceptors are sensory nerve endings located in the heart and vasculature that are stimulated by increased fluid pressure. Stimulation of baroreceptors causes impulses to be relayed via afferent pathways to nuclei in the brainstem that result in parasympathetic activation and sympathetic inhibition. Baroreflex stimulation may be brought about using a nerve cuff electrode placed around the aortic or carotid sinus nerve or using an intravascular electrode disposed near baroreceptors in the heart or pulmonary artery. Neural stimulation could similarly be delivered to other sympathetic/parasympathetic targets such as chemoreceptors and nerves innervating organs such as the kidney.

It has also been demonstrated in mammals that cardiac vagal discharge is blocked during respiratory inspiration. Neural stimulation of the vagus nerve, either directly or indirectly through a reflex, delivered during the inspiratory phase of respiration would therefore have little effect. In order to avoid unnecessarily draining the limited energy storage capacity of the battery, one embodiment of an implantable neural stimulation device as described herein is configured to deliver stimulation only during the expiratory phase of the respiratory cycle. (As the term is used herein, the "expiratory phase" should be taken to mean any part of the respiratory cycle during which there is no inspiration.) The device may incorporate a minute ventilation sensor for providing information regarding the onset and duration of inspiration. The neural target may be stimulated at a programmable duty cycle (e.g., stimulate for n seconds, off for m seconds). The neural stimulation duty cycle may be adjusted to compensate for the interruptions caused by inspiration in order to maintain an overall constant effective duty cycle. The neural stimulation duty cycle may also be adjusted to titrate a physiological variable (e.g., heart rate) to a programmable target. The device may be used to provide therapy for heart failure, acute myocardial infarction, angina, renal disease, and/or hypertension. The device may or may not be used in combination with a cardiac resynchronization device, defibrillator and/or pacemaker.

Exemplary Neural Stimulator Device

Figure 1:
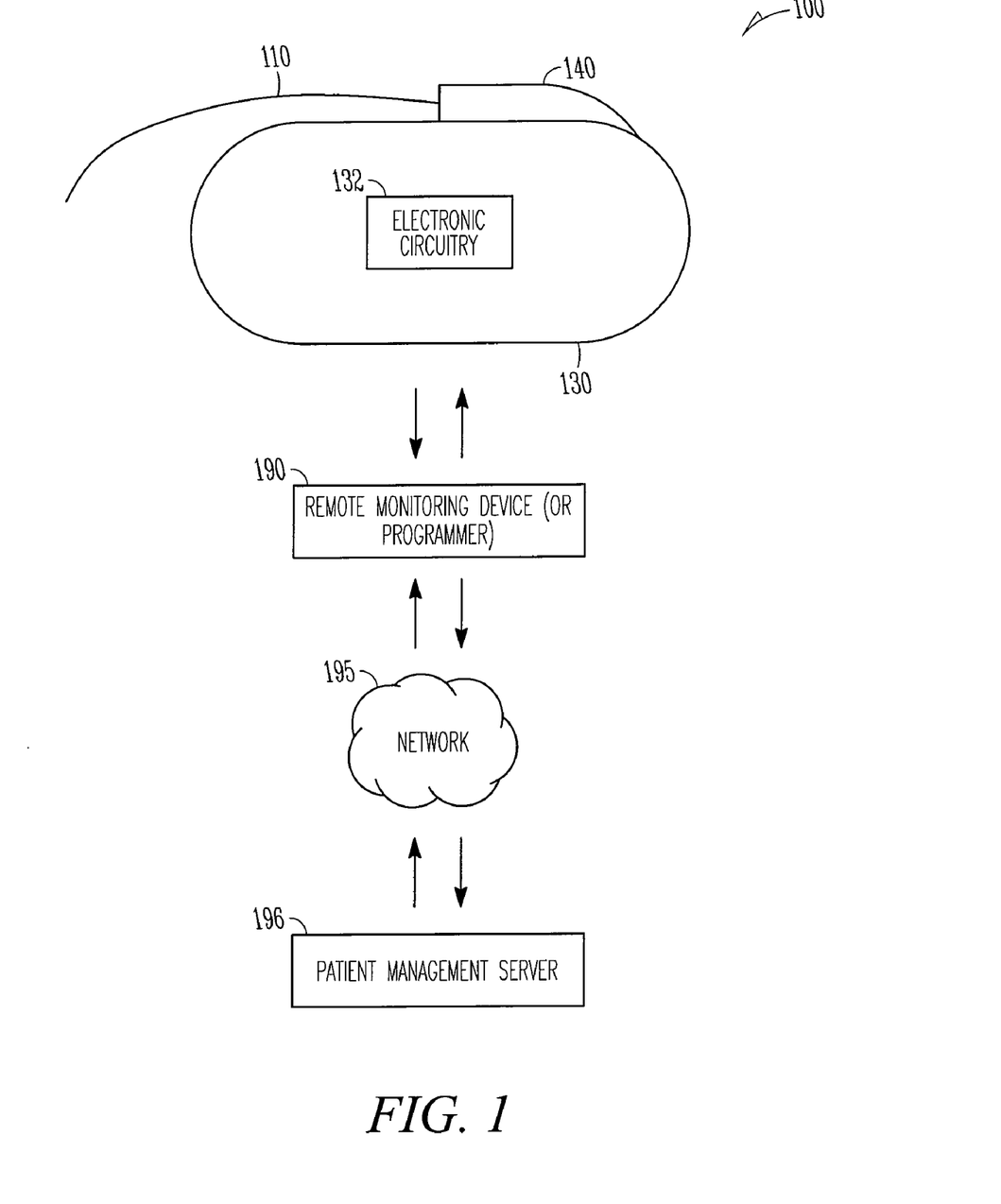
FIG. 1 illustrates a system for delivering neural stimulation.

FIG. 1 shows the components of an exemplary system for delivering neural stimulation. An implantable neural stimulation device 100 includes a hermetically sealed housing 130 that is placed subcutaneously or submuscularly in a patient's chest or other convenient location similar to a cardiac pacemaker. The housing 130 may be formed from a conductive metal, such as titanium, and may serve as an electrode for delivering electrical stimulation with a unipolar lead. A header 140, which may be formed of an insulating material, is mounted on the housing 130 for receiving one or more leads 110 which are electrically connected to the circuitry within the housing. Electrical pulse generation circuitry within the housing 130 is connected to a lead 110 which incorporates a bipolar or unipolar electrode at its distal end for stimulating nervous tissue. In one embodiment, the lead 110 is tunneled subcutaneously to a specific pre-ganglionic or post-ganglionic stimulation site near the vagus nerve or an afferent baroreceptor nerve. In another embodiment, the lead 110 is threaded intravascularly to dispose the stimulating electrode (s) near a target nerve. Contained within the housing 130 is the electronic circuitry 132 for providing the functionality to the device as described herein which may include a power supply, sensing circuitry, pulse generation circuitry, a programmable electronic controller for controlling the operation of the device, and a telemetry transceiver capable of communicating with an external programmer or a remote monitoring device 190. An external programmer wirelessly communicates with the device 100 and enables a clinician to receive data and modify the programming of the controller. A neural stimulation device may be configured to control the delivery of neural stimulation in an open-loop fashion via telemetry or in a closed-loop fashion based upon an assessment of autonomic balance performed by the device. A magnetically or tactilely actuated switch may also be provided that allows the patient to initiate or stop the delivery of neural stimulation pulses. A remote monitoring device that communicates via telemetry with the device 100 and may be further interfaced to a network 195 (e.g., an internet connection) for communicating with a patient management server 196 that allows clinical personnel at remote locations to receive data from the remote monitoring device as well as issue commands. The controller may be programmed such when particular conditions are detected by the monitoring circuitry (such as when a measured parameter exceeds or falls below a specified limit value), the device transmits an alarm message to the remote monitoring device and to the patient management server to alert clinical personnel.

Figure 2:
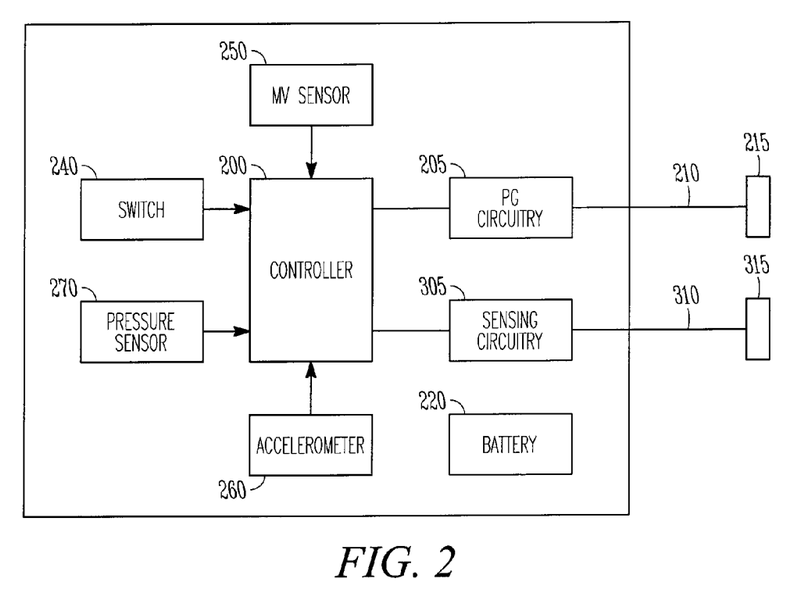
FIG. 2 is a block diagram of an implantable device for delivering neural stimulation.

FIG. 2 is a system diagram of exemplary electronic components contained within the housing 130 of the neural stimulator. A programmable electronic controller 200 is interfaced to pulse generation circuitry 205 and controls the output of neural stimulation pulses. The controller may also be interfaced to sensing circuitry for sensing cardiac activity or other physiological variables. The controller 200 may be made up of a microprocessor communicating with a memory, where the memory may comprise a ROM (read-only memory) for program storage and a RAM (random-access memory) for data storage. The controller could also be implemented by other types of logic circuitry (e.g., discrete components or programmable logic arrays) using a state machine type of design. As the term is used herein, the programming of the controller refers to either code executed by a microprocessor or to specific configurations of hardware components for performing particular functions. The controller includes circuitry for generating clock signals used to keep track of lapsed time intervals and deliver neural stimulation in accordance with a defined schedule. The pulse generation circuitry 205 may be similar to that used in cardiac pacemakers and delivers electrical stimulation pulses to a neural stimulation electrode 215 (or electrodes in the case of a bipolar lead) via the lead 210. A battery 220 also contained within the housing provides power to the device. A magnetically or tactilely actuated switch 240 interfaced to the controller 200 allows the patient to initiate and/or stop the delivery of neural stimulation pulses. Once begun, the neural stimulation pulses may continue to be delivered for a predetermined length of time or according to a predetermined schedule. The pulse frequency, pulse width, pulse amplitude, pulse polarity, burst duration, and bipolar/unipolar stimulation configuration in this embodiment are programmable parameters, the optimal settings of which depend upon the stimulation site and type of stimulation electrode. The device may also be equipped with different sensing modalities for sensing physiological variables affected by neural stimulation. The device may then be programmed to use these variables in controlling the delivery of neural stimulation. The device in FIG. 2 includes sensing circuitry 305 connected to an electrode 315 (or electrodes in the case of a bipolar lead) via the lead 310 which may be intravenously disposed in the heart for detecting cardiac electrical activity. The sensing circuitry 305 allows the device to measure heart rate and to compute parameters derived therefrom such as heart rate variability or heart rate turbulence for use in controlling the delivery of neural stimulation. Separate sensing channels may be provided for detecting both atrial and ventricular beats. For example, vagal stimulation slows the heart rate, and the device may be programmed to titrate the level of neural stimulation delivered in response to a detected change in heart rate. The device may also be programmed to titrate the level of neural stimulation delivered in response to a detected change in one or more other sensed or derived variables affected by the neural stimulation. For example, as neural stimulation may affect respiratory rate, the device also includes a minute ventilation sensor 250 and may be programmed to similarly titrate the level of neural stimulation delivered in response to a detected change in respiratory rate. An accelerometer 260 is also interfaced to the controller which enables the device to detect the patient's activity level as well as heart sounds, the intensity of which may be reflective of myocardial contractility. A pressure sensor could also be used for this purpose by measuring arterial dP/dt during systole. A pressure sensor 270 may also be provided for measuring the patient's blood pressure, where such a pressure sensor may be incorporated into a lead that is intravascularly disposed or may be an external device that communicates with the controller wirelessly via telemetry. The accelerometer 260 may also be used to detect coughing brought about by vagal stimulation. The device may then be programmed so that neural stimulation is decreased or stopped if persistent coughing by the patient is detected.

Combination Cardiac Device/Neural Stimulator

Implantable cardiac devices have been developed that provide appropriately timed electrical stimulation to one or more heart chambers in an attempt to improve the coordination of atrial and/or ventricular contractions in heart failure patients, termed cardiac resynchronization therapy (CRT). Ventricular resynchronization is useful in treating heart failure because, although not directly inotropic, resynchronization can result in a more coordinated contraction of the ventricles with improved pumping efficiency and increased cardiac output. Currently, a most common form of CRT applies stimulation pulses to both ventricles, either simultaneously or separated by a specified biventricular offset interval, and after a specified atrio-ventricular delay interval with respect to the detection of an intrinsic atrial contraction or delivery of an atrial pace. A neural stimulator such as described above may also be incorporated into an implantable cardiac device configured to deliver conventional bradycardia pacing, anti-tachyarrhythmia therapy, and/or CRT. It has also been found that CRT can be beneficial in reducing the deleterious ventricular remodeling which can occur in post-MI and heart failure patients as a result of changes in the distribution of wall stress experienced by the ventricles during the cardiac pumping cycle when CRT is applied to pre-excite particular areas of the ventricles. By pacing one or more sites in a ventricle, CRT provides pre-excitation of myocardial regions which would otherwise be activated later during systole and experience increased wall stress. The pre-excitation of the remodeled region relative to other regions unloads the region from mechanical stress and allows reversal or prevention of remodeling to occur.

Figure 3:
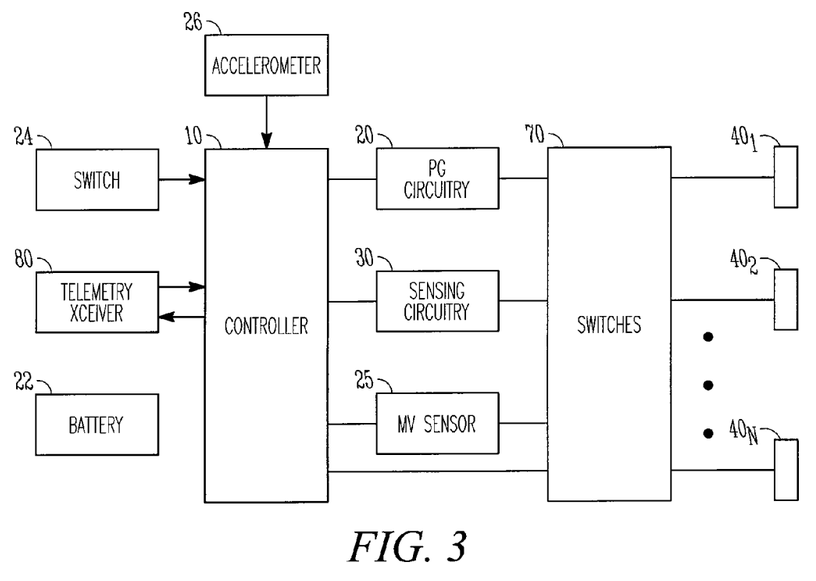
FIG. 3 is a block diagram of an implantable cardiac device with the capability of delivering neural stimulation.

FIG. 3 illustrates an embodiment of a neural stimulator that is incorporated into an implantable cardiac rhythm management device which has cardiac pacing and/or cardioversion/defibrillation functionality. The device is battery-powered and equipped with multiple sensing and pacing channels which may be physically configured to sense and/or pace the atria or the ventricles in a variety of pacing modes including conventional bradycardia pacing and cardiac resynchronization pacing. A battery 22 supplies power to the circuitry. The controller 10 controls the overall operation of the device in accordance with programmed instructions and/or circuit configurations and includes timing circuitry such as external clocks for implementing timers used to measure lapsed intervals and schedule events. Interfaced to the controller are sensing circuitry 30 and pulse generation circuitry 20 by which the controller interprets sensing signals and controls the delivery of paces in accordance with a pacing mode. An exertion level sensor (such as the accelerometer 26 or the minute ventilation sensor 25 shown in FIG. 3 or other sensor that measures a parameter related to metabolic demand) enables the controller to adapt the pacing rate in accordance with changes in the patient's physical activity. A telemetry transceiver 80 is interfaced to the controller which enables the controller to communicate with an external device such as an external programmer and/or a remote monitoring unit. A magnetically or tactilely actuated switch 24 is also shown as interfaced to the controller in this embodiment. The switch 24 may be operated by the patient similar to the operation of the embodiment illustrated in FIG. 2.

The sensing circuitry 30 receives atrial and/or ventricular electrogram signals from sensing electrodes and includes sensing amplifiers, analog-to-digital converters for digitizing sensing signal inputs from the sensing amplifiers, and registers that can be written to for adjusting the gain and threshold values of the sensing amplifiers. The pulse generation circuitry 20 delivers pacing pulses to pacing electrodes disposed in the heart and includes capacitive discharge or current source pulse generators, registers for controlling the pulse generators, and registers for adjusting pacing parameters such as pulse energy (e.g., pulse amplitude and width). The device allows adjustment of the pacing pulse energy in order to ensure capture of myocardial tissue (i.e., initiating of a propagating action potential) by a pacing pulse. The pulse generation circuitry may also include a shocking pulse generator for delivering a defibrillation/cardioversion shock via a shock electrode upon detection of a tachyarrhythmia.

A pacing channel is made up of a pulse generator connected to an electrode, while a sensing channel is made up of a sense amplifier connected to an electrode. Shown in the figure are electrodes $40_1$ through $40_N$ where N is some integer. The electrodes may be on the same or different leads and are electrically connected to a MOS switch matrix 70. The switch matrix 70 is controlled by the controller and is used to switch selected electrodes to the input of a sense amplifier or to the output of a pulse generator in order to configure a sensing or pacing channel, respectively. The device may be equipped with any number of pulse generators, amplifiers, and electrodes that may be combined arbitrarily to form sensing or pacing channels. One or more pacing channels may also be configured, by appropriate lead placement and pulse energy/frequency settings, for delivering electrical stimulation to stimulate sympathetic and/or parasympathetic nerves. For example, a lead with a stimulation electrode may be placed in proximity to the vagus nerve in order to stimulate that nerve and increase parasympathetic activity. The pulse generator for the neural stimulation channel outputs a train of neural stimulation pulses that may be varied by the controller as to amplitude, frequency, pulse width, and burst duration.

Pulse Generation Circuitry

Figure 4:
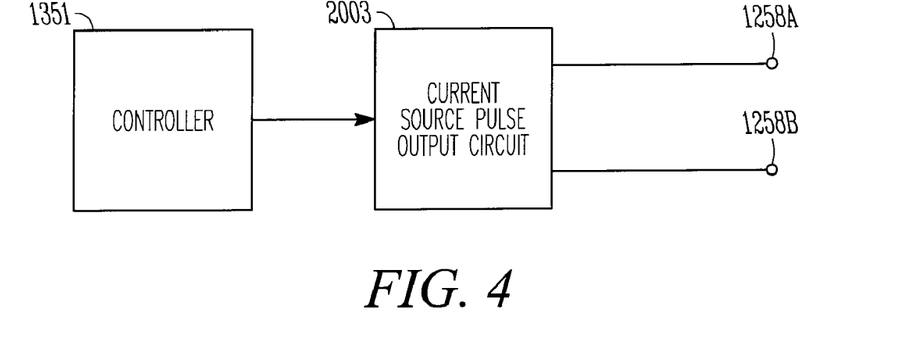
FIGS. 4 and 5 illustrate different embodiments of circuitry for delivering neural stimulation pulse trains.
Figure 5:
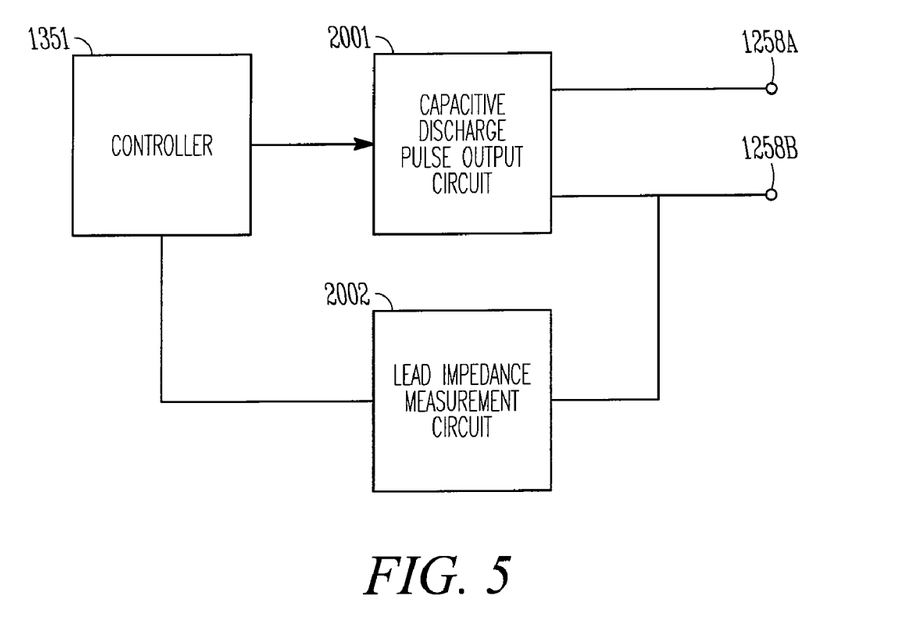

FIGS. 4 and 5 illustrate different embodiments of circuitry for delivering neural stimulation pulse trains as described above such as the pulse generators in FIG. 3 and FIG. 2. In FIG. 4, a current source pulse output circuit 2003 outputs current pulses between stimulation electrodes 1258A and 1258B in accordance with command inputs from the controller 1351. The command inputs from the controller which may be programmed by a user specify the frequency of the pulses, pulse widths, current amplitude, pulse polarity, and whether unipolar or bipolar stimulation is to be delivered. FIG. 5 illustrates another embodiment in which a capacitive discharge pulse output circuit 2001 is used to output voltage pulses between stimulation electrodes 1258A and 1258B in accordance with command inputs from the controller 1351. In this embodiment, the command inputs from the controller which may be programmed by a user specify the frequency of the pulses, pulse widths, voltage amplitude, pulse polarity, and whether unipolar or bipolar stimulation is to be delivered. In order for the controller to specify a voltage amplitude that results in a desired current amplitude for the pulses, the lead impedance may be measured by lead impedance measurement circuit 2002. The output capacitor of the pulse output circuit may then be charged to the appropriate voltage for each pulse. In order to monitor the lead impedance, the controller is programmed to periodically, or upon command from a user via telemetry, charge the output capacitor to a known voltage level, connect the output capacitor to the stimulation leads to deliver a stimulation pulse, and measure the time it takes for the capacitor voltage to decay by a certain amount (e.g., to half of the initial value). In order to minimize patient discomfort, the lead impedance procedure should be performed using as low a voltage as possible. In one embodiment, the controller is programmed to use a first voltage amplitude (e.g., 1 volt) and then compare the measurement count (i.e., the capacitor decay time) to a specified minimum value CntZMin. If the measurement count is below CntZMin, the current delivered during the test is deemed too small for the measurement to be accurate. A second measurement pulse is then delivered at a higher second voltage (e.g., 2 volts). If that count is again below CntZMin, a third measurement pulse is delivered at a still higher third voltage (e.g., 4 volts). With a typical stimulation lead, this procedure limits the measurement current to between roughly 1 mA and 0.6 mA.

Controlled Delivery of Neural Stimulation

In an exemplary embodiment, an implantable neural stimulation device such as described above is configured to alternate between operating in either a neural stimulating (NS) state or a non-neural stimulating (non-NS) state. When in the NS state, the device delivers neural stimulation according to programmed stimulation parameters. In the non-NS state, the device delivers no neural stimulation. The durations of the NS and non-NS states thus define a neural stimulation duty cycle. For example, the device could be programmed to deliver a burst of neural stimulation pulses in the NS state for 10 seconds and then enter the non-NS state for 50 seconds in which no stimulation pulses are delivered. As described below, the device may be programmed to deliver neural stimulation in a closed-loop manner by varying the duty cycle of the NS state and/or varying one or more other stimulation parameters in response to one or more measured physiological variables related to the patient's autonomic balance and/or affected by neurostimulation therapy. Examples of such measured variables include heart rate, PR interval, respiratory rate, blood pressure, and activity level. Since autonomic balance also varies in accordance with circadian rhythms, another possible measured physiological variable is the time of day. In the embodiments described below, reference is made to a generic physiological variable PV that may represent one of more such variables. Also, the physiological variable PV may be an instantaneous measurement or an average of previously measured values over some specified period of time. The physiological variable PV may also represent measurement of a single variable or a composite function of a plurality of variables. For example, PV may be a weighted average of heart rate, blood pressure, activity level, and respiratory rate.

Figure 6:
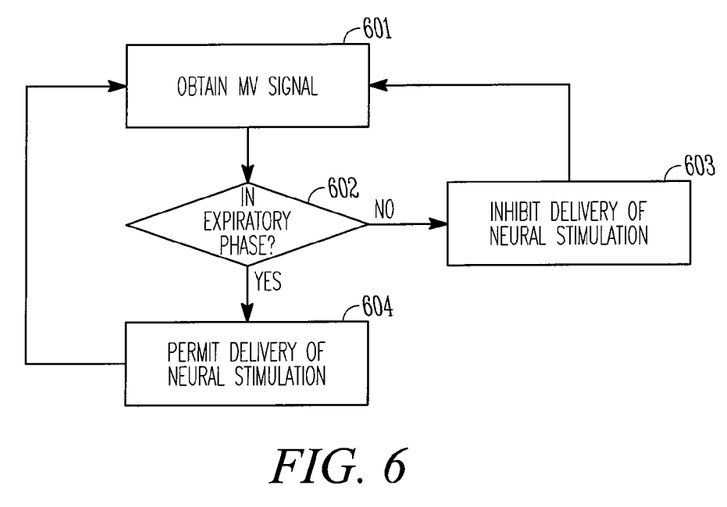
FIG. 6 illustrates an algorithm delivering neural stimulation pulses during expiration.

As noted above, cardiac vagal discharge is blocked during respiratory inspiration. Accordingly, in one particular embodiment, an implantable neural stimulation device is configured to deliver neural stimulation only during the expiratory phase of the respiratory cycle. FIG. 6 illustrates an exemplary algorithm that could be executed by the device controller to deliver such neural stimulation. The algorithm would execute concurrently with the neural stimulation duty cycle. At step 601, the device obtains a signal from the minute ventilation sensor (or other sensor providing an indication of respiratory activity) and determines if the patient's respiration is currently in the expiratory phase at 602. If the expiratory phase is not present, delivery of neural stimulation is inhibited at step 603. The device then loops back to step 601. If the expiratory phase is present, the device permits neural stimulation delivery at step 604 and then returns to step 601.

Figure 7:
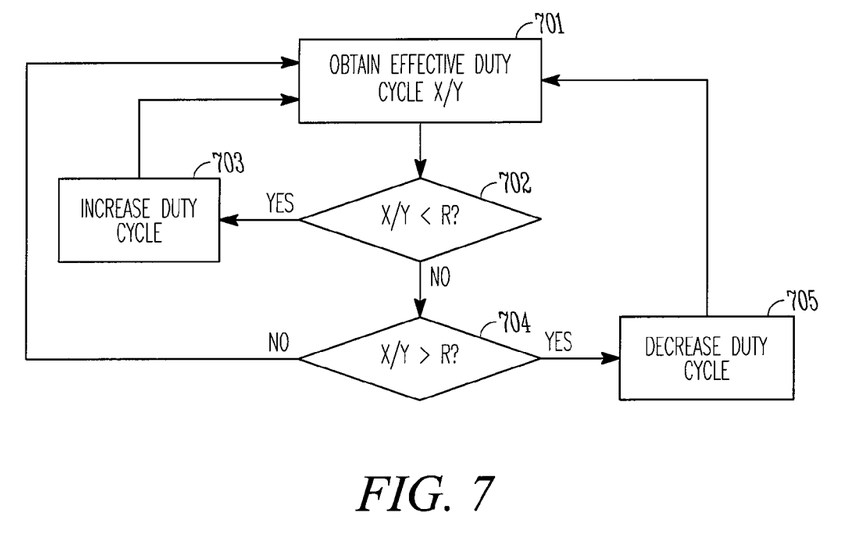
FIGS. 7 and 8 illustrate algorithms for adjusting the neural stimulation duty cycle.

In an embodiment in which delivery of neural stimulation is inhibited by the respiratory cycle such as illustrated by FIG. 6, the programmed neural stimulation duty cycle will be reduced to some effective overall duty cycle due to the intermittent interruption of the stimulation pulses. The controller may be configured to compensate for this by measuring the cumulative duration of delivered stimulation pulses over some period of time and adjusting the stimulation duty cycle so that a desired effective overall duty cycle is achieved. FIG. 7 illustrates an exemplary algorithm that could be periodically executed by the controller to perform this function. The device in this embodiment is programmed with a duty cycle of M seconds in the NS state and T seconds in the non-NS state. The device is also configured to maintain a record of the time during which neural stimulation pulses have actually been delivered. At step 701, the device obtains the cumulative duration X of the neural stimulation that has been delivered over some period of time Y. The ratio X/Y is thus the effective overall duty cycle of neural stimulation as actually delivered by the device. The device then compares the ratio X/Y to a programmed value R that represents the desired overall duty cycle. If the ratio X/Y is less than R (or less than R by some specified margin) as determined at step 702, the device increases the duration M of the NS state and/or decreases the duration T of the non-NS state at step 703 and returns to step 701. If the ratio X/Y is greater than R (or greater than R by some specified margin) as determined at step 704, the device decreases the duration M of the NS state and/or increases the duration T of the non-NS state at step 705 and returns to step 701. Otherwise, the device makes no changes to the duty cycle and returns to step 701 to continue execution of the algorithm.

Figure 8:
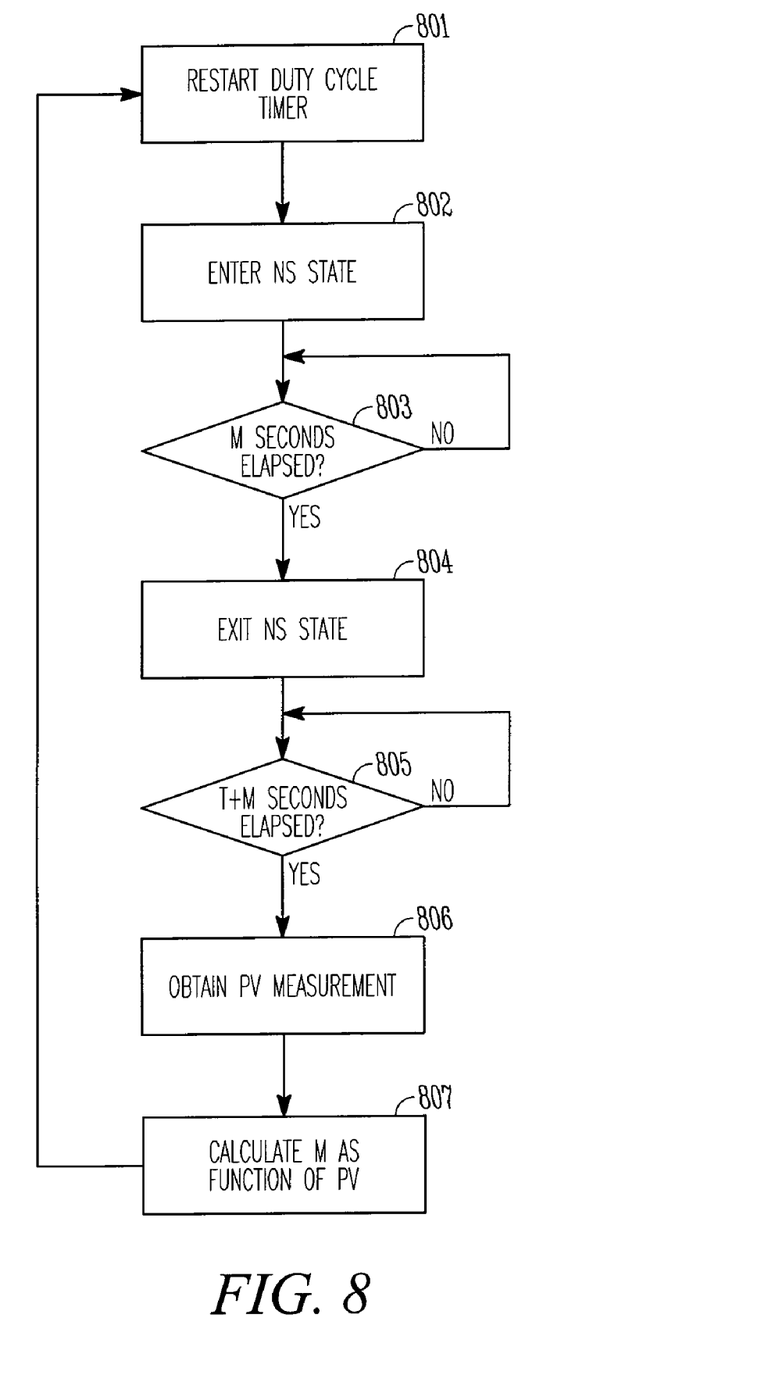

In another embodiment, the controller is programmed to adjust the neural stimulation duty cycle in accordance with measurement of physiological variable measurement related to the patient's autonomic balance. For example, the duty cycle for delivering vagal stimulation may be increased upon measurement of a physiological variable that indicates an increased sympathetic tone. FIG. 8 illustrates an exemplary algorithm that could be executed by the controller to implement such duty cycling. The algorithm begins after the device has exited the neural stimulation state and is in a non-neural stimulation state where no pre-excitation pacing is being delivered. At step 801, a duty cycle timer is started which counts from zero to T+M seconds (or other unit of time) where T and M are specified values corresponding to the duration of the non-NS and NS states, respectively. At step 802, the device enters the NS state and begins delivering neural stimulation. At step 803, while continuing to operate in the NS state, the device monitors the duty cycle timer until M seconds have elapsed, at which point the device exits the NS state at step 804. The device then monitors the duty cycle timer at step 805 until T+M seconds have elapsed. The device then obtains a physiological variable measurement PV at step 806. The value of M is then calculated as a function of the physiological variable measurement PV at step 807. The function for mapping the physiological variable measurement to a value for M could be simple, such as where the value of M alternates between two values according to the value of the physiological variable measurement, or more complicated. In the latter instance, the function could be implemented as a look-up table. Either in addition to or instead of adjusting the duty cycle at step 807, the values of one or more other stimulation parameters could similarly be calculated as functions of the physiological variable measurement. Examples of such stimulation parameters include pulse width, pulse frequency, and pulse amplitude.

The device may also be configured so that neural stimulation is either started or stopped upon detecting a specified entry or exit condition, respectively. Examples of exit conditions are actuation of a patient-actuated switch, reception of a telemetry command to cease neural stimulation, or a physiological variable reaching some specified value indicating that it would be dangerous or otherwise undesirable to deliver neural stimulation. The device may also be configured so that neural stimulation may only be delivered if permitted by the patient as indicated by actuation of the patient actuated switch, the switch actuation thus serving as an entry condition. Entry and exit conditions could be programmed directly as a separate algorithm executed by the device controller. Another way to implement entry and exit conditions is to consider such conditions as physiological variable measurements and incorporate them into the look-up table used to change the neural stimulation duty cycle as described above with respect to FIG. 8. For example, the look-up table could contain an entry for a command to cease neural stimulation (either via telemetry or the patient-actuated switch) so that if such a command has been issued, the neural stimulation duty cycle is turned off (i.e., the duty cycle is adjusted so that no stimulation is delivered by setting the value of M in FIG. 8 to zero). As noted above, autonomic balance exhibits a circadian variation, and the time of day can thus be considered as a physiological variable measurement. The look-up table could be constructed such that the neural stimulation duty cycle is turned on or off according to the time of day. In one example, the look-up table is constructed so that neural stimulation is only delivered at night when the patient is expected to be sleeping. The look-up table could also contain another condition to confirm that the patient is sleeping such as the measured activity level being below some specified value.

Although the invention has been described in conjunction with the foregoing specific embodiments, many alternatives, variations, and modifications will be apparent to those of ordinary skill in the art. Such alternatives, variations, and modifications are intended to fall within the scope of the following appended claims.

What is claimed is:

1. An implantable device for delivering neural stimulation, comprising:
    a pulse generator for outputting neural stimulation pulses to one or more stimulation electrodes connected to the pulse generator for delivering electrical stimulation to a selected neural site, wherein the stimulation electrodes are configurable for delivering vagal stimulation to a patient;
    a controller connected to the pulse generator for controlling the output of neural stimulation pulses;
    wherein the controller is programmed to alternate between a neural stimulation state in which neural stimulation pulses are delivered and a non-neural stimulation state in which no neural stimulation pulses are delivered;
    wherein the controller is programmed to alternate between the neural stimulation state and the non-neural stimulation state according to a programmed duty cycle that specifies durations for each state;
    a respiratory sensor connected to the controller for enabling detection of inspiratory and expiratory respiratory phases;
    wherein the controller is programmed to permit neural stimulation pulses to be delivered when in the neural stimulation state only during the expiratory respiratory phase; and,
    wherein the controller is further programmed to maintain a record of the cumulative duration of neural stimulation and derive an effective overall duty cycle, adjust the programmed duty cycle to increase the duration of the neural stimulation state and/or decrease the duration of the non-neural stimulation state if the effective overall duty cycle is less than the desired overall duty cycle, and adjust the programmed duty cycle to decrease the duration of the neural stimulation state and/or increase the duration of the non-neural stimulation state if the effective overall duty cycle is more than the desired overall duty cycle.

2. The device of claim 1 further comprising:
    a patient-actuated switch; and,
    wherein the controller is programmed to permit neural stimulation pulses to be delivered when in the neural stimulation state only upon detecting actuation of the patient-actuated switch.

3. The device of claim 1 further comprising:
    one or more sensing modalities for measuring one or more physiological variables related to a patient's autonomic balance;
    wherein the controller is programmed to adjust the amount of neural stimulation delivered in accordance with the one or more measured physiological variables.

4. The device of claim 3 wherein the controller is further programmed to adjust the durations of the neural stimulation and non-neural stimulation states in accordance with the physiological variable measurement.

5. The device of claim 3 wherein the physiological variable measurement is an average of the signal related to a patient's physiological variable as generated over a specified period of time.

6. The device of claim 3 wherein the sensing modality is a cardiac sensing channel for sensing cardiac electrical activity and the measured physiological variable is heart rate.

7. The device of claim 3 wherein the sensing modality is a sensor for sensing respiratory activity and the measured physiological variable is respiratory rate.

8. The device of claim 3 wherein the sensing modality is an accelerometer and the measured physiological variable is activity level.

9. The device of claim 3 wherein the sensing modality is a pressure sensor and the measured physiological variable is blood pressure.

10. The device of claim 3 wherein the controller is programmed to adjust the amount of neural stimulation in accordance with a weighted average of measured physiological variables.

11. The device of claim 3 wherein the controller is programmed to deliver neural stimulation only during a specific time of day.

12. The device of claim 11 wherein the controller is programmed to deliver neural stimulation only at a time of day when a patient is expected to be sleeping.

13. The device of claim 12 wherein the controller is further programmed to deliver neural stimulation only if the patient's measured activity level is below a specified value.

14. A method for operating an implantable device to deliver neural stimulation, comprising:
    alternating between a neural stimulation state and a non-neural stimulation according to a programmed duty cycle that specifies a duration for each state;
    delivering bursts of neural stimulation pulses to a vagal stimulation site of a patient when the device is in the neural stimulation state;
    detecting inspiratory and expiratory respiratory phases of the patient;
    permitting neural stimulation pulses to be delivered when in the neural stimulation state only during the expiratory respiratory phase; and,
    maintaining a record of the cumulative duration of neural stimulation and deriving an effective overall duty cycle, adjusting the programmed duty cycle to increase the duration of the neural stimulation state and/or decrease the duration of the non-neural stimulation state if the effective overall duty cycle is less than the desired overall duty cycle, and adjusting the programmed duty cycle to decrease the duration of the neural stimulation state and/or increase the duration of the non-neural stimulation state if the effective overall duty cycle is more than the desired overall duty cycle.

15. The method of claim 14 further comprising permitting neural stimulation pulses to be delivered when in the neural stimulation state only upon detecting actuation of a patient-actuated switch.

16. The method of claim 14 further comprising:
measuring one or more physiological variables related to the patient's autonomic balance;
adjusting the amount of neural stimulation delivered in accordance with the one or more measured physiological variables.

17. The method of claim 14 further comprising adjusting the durations of the neural stimulation and non-neural stimulation states in accordance with the physiological variable measurement.

18. The method of claim 14 further comprising delivering neural stimulation only during a specific time of day.

19. The method of claim 18 further comprising delivering neural stimulation only at a time of day when a patient is expected to be sleeping.

20. The method of claim 19 further comprising delivering neural stimulation only if the patient's measured activity level is below a specified value.

\* \* \* \* \*